(12) United States Patent
Hussain et al.

(10) Patent No.: US 6,369,058 B1
(45) Date of Patent: Apr. 9, 2002

(54) BRAIN DELIVERY OF FOLIC ACID FOR THE PREVENTION OF ALZHEIMER'S DISEASE AND STROKE

(75) Inventors: Anwar A. Hussain; Lewis W. Dittert; Ashraf Traboulsi, all of Lexington, KY (US)

(73) Assignee: New Millennium Pharmaceutical Research Inc., Lexington, KY (US)

( * ) Notice: Subject to any disclaimer, the term of this patent is extended or adjusted under 35 U.S.C. 154(b) by 0 days.

(21) Appl. No.: 09/482,910

(22) Filed: Jan. 14, 2000

Related U.S. Application Data

(60) Provisional application No. 60/118,645, filed on Feb. 4, 1999.

(51) Int. Cl.$^7$ .................. A61K 31/495; A61K 31/50
(52) U.S. Cl. ............................................... 514/249
(58) Field of Search ........................... 514/152.02, 249

(56) References Cited

U.S. PATENT DOCUMENTS 5,891,875 A * 4/1999 Hipskind et al. ........ 514/235.2

* cited by examiner

*Primary Examiner*—Theodore J. Criares
(74) *Attorney, Agent, or Firm*—Burns, Doane, Swecker & Mathis, L.L.P.

(57) ABSTRACT

This invention provides a method of rapidly and reliably delivering folic acid, alone or in combination with other compounds, to the systemic circulation by administration via the nasal route to produce rapid onset of beneficial effects in the treatment or prevention of Alzheimer's Disease and stroke. The present invention further provides intranasal pharmaceutical compositions comprising folic acid, and/or pharmaceutically acceptable salts thereof in a variety of unique pharmaceutical dosage forms, with and without other anti-Alzheimer's or anti-stroke compounds.

6 Claims, No Drawings

BRAIN DELIVERY OF FOLIC ACID FOR THE PREVENTION OF ALZHEIMER'S DISEASE AND STROKE

This application claims the benefit of Provisional application No. 60/118,645 filed Feb. 4, 1999.

BACKGROUND OF THE INVENTION

1. Field of the Invention

This invention relates to a method for greatly accelerating the rate of delivery of folic acid, and derivatives thereof, to the central nervous system by administration via the nasal route to provide extremely rapid response in the prevention or treatment of Alzheimer's disease or stroke in a patient in need of such prevention or treatment. This method also provides for direct absorption of folic acid into the central nervous system, bypassing the metabolic enzymes circulating in the bloodstream that would otherwise destroy folic acid administered by another route.

2. Description of the Related Art

Alzheimer's Disease

Alzheimer's Disease (AD) is a slowly debilitating neurodegenerative chronic illness that may progress for a decade or longer before death ensues. The disease often strikes later in life. This is evidenced by the fact that half of those over the age of 80 years are afflicted with the disorder. At present, it is the fourth leading cause of adult deaths in the US alone, at an annual cost of approximately $100 billion. As the longevity of the world's population increases, this disease will become an even greater problem unless a better understanding of the disease process and its management is achieved.

Alois Alzheimer is credited with being the first to diagnose what is now known as Alzheimer's disease (AD). In 1906, Alzheimer reported a case of what he termed "presenile dementia" in a 51 year old patient at a psychiatric meeting in Southwest Germany. He recognized certain characteristics that he felt differentiated it from the usual diagnosis of dementia. First was the early onset of the disease in an otherwise healthy young woman. More importantly, however, were the histological changes he found in sections of brain tissue from the patient. Alzheimer described seeing amyloid (starch-like) plaques and coarse-fibered proliferations of neurofibrils under the microscope. Several other researchers in years following reported similar findings of presenile dementia, and in 1910 a textbook of psychiatric disorders defined this form of dementia as "Alzheimer's disease." The eponym was adopted in the literature and became the standard. It is perhaps fitting since Alzheimer's original observations are still the main criteria of diagnosis for the disease.

The plaques and neurofibrils described by Alzheimer, which are today called senile plaques and neurofibrillary tangles (NFT), are used as a definitive diagnosis of AD. The plaques and tangles are seen primarily in the hippocampus, amygdala, and the cerebral cortex. Evidence for either a molecular or immunological disease origin may be found in the plaques and tangles, depending upon a researcher's point of reference. From a molecular perspective, the initial identification of specific mutations within the amyloid precursor protein (APP) and the presence of $A\beta$ (a derivative of APP) in plaques points to a unique protein cause for AD. Also, several other protein players have since entered the AD arena.

These include the already mentioned major constituent of NFTs, tau, as well as three recent additions. Presenilins 1 and 2 are integral membrane proteins coded for on different chromosomes, that when mutated are responsible for up to 90% of the cases of autosomal dominant early-onset familial Alzheimer's disease (FAD). Although FAD accounts for an only 10%, of all cases of AD, there is evidence of in interaction between the presenilins and APP. Therefore, even normal forms of the proteins may play a role in the far more common sporadic AD. Finally, a specific isoform of apolipoprotein E (apoE), apoE4, has been shown to be a strong genetic risk factor for AD. People carrying two copies of the of the E4 isoform have a statistically greater risk of developing late-onset and in vitro experiments have shown that apoE is capable of binding to $A\beta$.

The histopathological investigations into AD also point to the immune response having an important role in disease progression. The presence of activated microglia, reactive astrocytes, acute phase proteins, and complement factors within and around neuritic plaques are all signs of in inflammatory response. It is known that AP is of binding specifically to C1q, which can trigger activation of the classical pathway of the complement cascade in an antibody-independent manner. Deposition of complexes and formation of immunomodulators by the cascade have been credited with activating the microglia—macrophages of the brain—which in turn cause a progression and maintenance of the inflammation. Local tissue destruction follows, along with a further persistence ind increase in inflammation. The important unresolved question in this model is whether $A\beta$ deposition and plaque formation or activation of complement and inflammation come first.

Prior Modes of Treatment of Alzheimer's Disease

A major approach to the treatment of AD has involved attempts to augment the cholinergic function of the brain. An early approach was the use of precursors of acetylcholine synthesis, such as choline chloride and phosphatidyl choline (lecithin). Although these supplements are generally well tolerated, randomized trials have failed to demonstrate any clinically significant efficacy. Direct intracerebroventricular injection of cholinergic agonists such as bethanacol appears to have some beneficial effects, although this requires surgical implantation of a reservoir connecting to the subarachnoid space and is too cumbersome and intrusive for practical use. A somewhat more successful strategy has been the use of inhibitors of acetylcholinesterase (AChE), the catabolic enzyme for acetylcholine. Physostigmine, a rapidly acting, reversible AChE inhibitor, produces improved responses in animal models of learning, and in patients with AD some studies have demonstrated mild transitory improvement in memory following physostigmine treatment. The use of physostigmine has been limited because of its short half-life and tendency to produce symptoms of systemic cholinergic excess at therapeutic doses.

Recently, the acridine derivative tacrine (COGNEX®;1, 2,3,4-tetrahydro-9-aminoacridine) has been approved by the United States Food and Drug Administration for the treatment of dementia in AD. Tacrine was first synthesized nearly fifty years ago, and the pharmacology of this agent has been the subject of numerous studies. It is a potent centrally acting inhibitor of AChE. The side effects of tacrine may be significant and dose-limiting: abdominal cramping, nausea, vomiting, and diarrhea are observed in up to one-third of patients receiving therapeutic doses. Tacrine may also cause hepatotoxicity, as evidenced by the elevation of serum transaminases observed in up to 20% of patients treated. Because of the relatively small improvements that result from tacrine treatment and the significant side-effect profile, its clinical usefulness is limited.

Alzheimer's disease and stroke are among the most difficult conditions to treat because it is essential to deliver therapeutically effective quantities of required drugs to the brain. Recently, folic acid has been found to be useful in the treatment of these conditions.

Recent research has indicated that folic acid supplements substantially reduce the incidence of Alzheimer's disease and stroke in healthy aging subjects. Folate is necessary for DNA synthesis and repair. Sufficient amounts of folate are not readily available from food, and very small quantities of ingested folate ever reach the brain. Synthetic folic acid is more orally bioavailable than natural folate, but even synthetic folate may not be efficiently transported across the blood-brain barrier to be effective in the treatment of Alzheimer's disease and stroke. A more reliable dosage form and route of administration is needed to ensure that sufficient quantities of this vitamin are delivered to the brain.

Stroke

The brain is highly vulnerable to disturbance of the blood supply; anoxia and ischemia lasting only seconds (called "Transient Ischemic Attack" or "TIA") can cause neurological symptoms and within minutes can cause irreversible neuronal damage.

Blood flow to the central nervous system must efficiently deliver oxygen, glucose, and other nutrients and remove carbon dioxide, lactic acid, and other metabolic products. The cerebral vasculature has unique anatomical and physiological features that serve to protect the brain from circulatory compromise. When these protective mechanisms fail the result is a stroke. Broadly defined, the term stroke, or cerebrovascular accident, refers to the neurological symptoms and signs, usually focal and acute, that result from diseases involving blood vessels.

Prior Modes of Treatment of Stroke

When a TIA has been diagnosed, the goal of therapy is to prevent a stroke. If infarction has occurred, the most important objective of therapy is to prevent worsening of the stroke.

ANTICOAGULANT THERAPY. Heparin prevents clot propagation and formation by potentiating antithrombin IIII activity. The heparin-antithrombin III complex inactivates thrombin and other coagulation enzymes including factors X, XII, XI, and IX. Heparin also inhibits proliferation of vascular smooth muscle and platelet activation. Heparin therapy is sometimes advocated when a tightly stenotic internal carotid artery or an impending or completed carotid or middle cerebral artery occlusion is suspected. When a major carotid territory stroke is suspected, the middle cerebral artery stem (lenticulostriate) and peripheral (cortical surface) territory may both be infarcted. In this setting, acute anticoagulation is usually avoided because preventing further stroke is not an issue and hemorrhage into infarction in the lenticulostriate territory is a possible complication. Generally, heparin is given as a continuous intravenous infusion to raise the partial thromboplastin time to 1.5 to 2.5 times control. A 1000- to 10,000-unit bolus may be given prior to initiating the continuous infusion.

Sodium warfarin (Coumadin) inhibits the activation of vitamin-K, the essential cofactor in the activation of the vitamin K-dependent coagulation proteins. Chronic oral anticoagulation with sodium warfarin is considered in patients when an embolic or low-flow TIA or stroke is related to carotid siphon or middle cerebral stem stenosis. It is also considered for a 6-month trial to prevent subsequent embolism when the internal carotid artery is known to have been occluded recently. It is well established that the risk of hemorrhage is directly related to the intensity of anticoagulation. Therefore, low-intensity warfarin anticoagulation (prothrombin time ration 1.2 to 1.5 times control or international normalized ratio 1.5 to 2.7 or 2 to 3) is usually used. When the standard medical contraindications are present, antiplatelet therapy becomes the only option.

ANTIPLATELET THERAPY. Studies of the effect of antiplatelet agents on the natural history of TIAs and minor stroke all suffer from a lack of precise understanding of the pathophysiologic condition underlying the ischemic event. Aspirin has been the most widely studied antiplatelet agent. Paradoxically, aspirin has dual effects: it inhibits platelet formation of thromboxane $A_2$, a platelet-aggregating, vasoconstricting prostaglandin, but it also inhibits the formation of prostacyclin, an antiaggregating, vasodilating prostaglandin derived from endothelial cells. Aspirin in low doses predominantly inhibits the production of thromboxane $A_2$; therefore, many physicians recommend aspirin in doses of 300 mg or less per day.

Dipyridamole acts by inhibiting platelet phosphodiesterase, which is responsible for the breakdown of cyclic adenosine monophosphate (AMP). The resulting elevation in cyclic AMP inhibits the aggregation of platelets. Ticlopidine is thought to inhibit platelet binding to fibrinogen, and recent studies have shown it to be comparable to aspirin in preventing stroke in patients with TIAs or stroke. Ticlopidine has the disadvantage of incurring a small risk of leukopenia, diarrhea, and rash. It is recommended for use as an antiplatelet agent only if aspirin is contraindicated or fails.

OTHER THERAPIES. Other pharmacological therapies useful in reducing stroke size include the administration of calcium channel antagonists (e.g., bepridil; calciseptine; cyproheptadine; diltiazem; flunarizine; fluspirilen; HA-1077; loperamide; nicardipine; nifedipine; niguldipine; nimodipine; nitrendipine; pimozide; ryanodine; verapamil), and administration of glutamate receptor antagonists (specifically the NMDA subtype) (e.g., AP3, (±)-; AP4, (±)-; AP5, (±)-; AP5, D(−)-; AP7, (±)-; AP7, D(−)-; CGS 19755; 7-chlorokynurenic acid; CPP, (±)-; CPP,D-; dextromethorphan; dextrorphan; 5,7-dichlorokynurenic acid; 6,7-dichlorquinoxaline-2,3-dione (DCQX); 5,5-dimethyl-1-pyrroline-N-oxide; 5-fluroindole-2-carboxylic acid; HA-966, (±)-; HA-966, R(+)-; HA-966, S(−)-; ketamine; kynurenic acid; MDL 105,519; memantine; MK-801; 1-napthyl-acetyl spermine; pentamidine isethionate).

SUMMARY OF THE INVENTION

A major object of the present invention is to provide a method for safely and conveniently administering folic acid to a patient in need of prevention or treatment of stroke or Alzheimer's disease, in order to produce a rapid and reliable response. The method comprises the intranasal administration of an effective amount of folic acid to a patient suffering from, or at risk for, stroke or Alzheimer's disease.

The objective of the present invention is to improve the rate of delivery of folic acid to the central nervous system by administering folic acid via the nasal route in order to speed the onset of effect and reduce the dose required for its beneficial effect. Intranasal delivery will improve drug bioavailability by direct absorption into the central nervous system, thereby avoiding extensive first-pass metabolism which may significantly lower the plasma concentrations of folic acid when it is administered via another route. As a result, small doses of folic acid, or derivatives thereof, can be administered which will result in fewer side effects, and the drug will be more tolerable and more effective in patients suffering from stroke or Alzheimer's disease. Importantly, since folic acid is rapidly effective following intranasal administration, establishment of an ideal dose for a particular patient is greatly facilitated.

Intranasal dosage forms containing folic acid in combination with other drugs used in the treatment of stroke and/or Alzheimer's disease may also be employed in the practice of the present invention.

With the foregoing and other objects, advantages and features of the invention that will become hereinafter apparent, the nature of the invention is further explained in the following detailed description of the preferred embodiments of the invention and in the appended claims.

DETAILED DESCRIPTION OF THE PREFERRED EMBODIMENTS OF THE INVENTION

Thus, the present inventors have discovered a novel method for the delivery of folic acid (N-[4-[[(2-Amino-1,4-dihydro-4-oxo-6-pteridinyl)methly] amino]benzoyl]-L-glutamic acid; pteroylglutamic acid), or derivatives thereof, to a patient in need of such treatment, comprising the intranasal administration of folic acid. This method offers significant clinical advantages over the prior art.

More specifically, the inventors sought to provide a rapid, reliable, safe, effective and convenient treatment for Alzheimer's disease or stroke comprising administering folio acid to a patient in need of such treatment, which comprises the administration of folio acid intranasally, thus providing rapid response compared to prior art methods of treatment of Alzheimer's disease or stroke while avoiding the side-effects associated with oral dosage forms. Specifically, smaller doses of folio acid can be administered through the nasal route, thus resulting in fewer side effects. By using the method of the present invention, which produces an rapid response, the drug will become more tolerable and more effective in treating patients suffering from Alzheimer's disease or stroke.

More particularly, the present invention concerns the intranasal administration of folic acid, which has the chemical structure of formula (I):

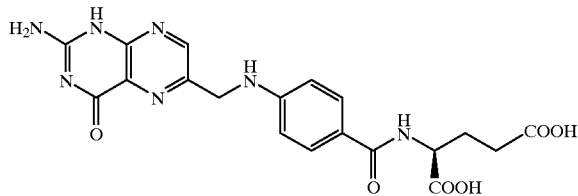

(I)

or a pharmaceutically acceptable salt thereof, or a pharmaceutical composition containing said compound. Preferred pharmaceutically acceptable salts of folio acid for use in the present invention include, but are not limited to, folic acid sulfate and folic acid phosphate. Such pharmaceutical compositions may be a medicament for the treatment of Alzheimer's disease or stroke in an animal, particularly a mammal, including a human. Alternatively, such pharmaceutical compositions may be a medicament for the prevention of Alzheimer's disease or stroke in an animal, particularly a mammal, including a human.

The present inventors have found that intranasal administration of folic acid effectively results in complete and very rapid absorption of these compounds into the central nervous system (CNS). Intranasal administration of folic acid is more effective than other routes of administration, because it permits absorption of folic acid directly into the central nervous system, bypassing the metabolic enzymes present in the circulation, the gastrointestinal tract, and liver. Moreover, intranasal formulations of folic acid may be conveniently and painlessly self-administered by the patient. Intranasal administration can be employed at far lower doses than oral administration, thereby allowing a decreased incidence of side effects.

According to the present invention, folic acid may be administered either as a free base, or in the form of a pharmaceutically acceptable salt thereof.

A still further aspect of this invention is a pharmaceutical composition of matter that comprises folic acid, or derivatives thereof, as described above, and/or pharmaceutically acceptable salts thereof, and pharmaceutically acceptable carriers therefor.

For therapeutic use in the prevention of treatment of Alzheimer's disease or stroke, folic acid or salts thereof, can be conveniently administered in the form of a pharmaceutical composition containing folic acid, or its salt, and a pharmaceutically acceptable carrier therefor. Typically, the carrier may be a liquid, solution, gel, or combinations thereof. In a preferred embodiment, the carrier is a pharmaceutically acceptable aqueous solution. Such compositions may require the use of one or more solubilizing agents to both effect dissolution of the drug(s) and/or keep them in aqueous solution. Suitable applications of solubilizing agents are exemplified below. Compositions according to the present invention may be prepared in accordance with accepted pharmaceutical practice, for example, as described in *Remington's Pharmaceutical Sciences*, seventeenth edition, ed. Alfonso R. Gennaro, Mack Publishing Company, Easton, Penn., Eighteenth edition (1990), which is hereby incorporated by reference.

Folic acid or its salt may be formulated together with the carrier into any desired unit dosage form. Unit dosage forms such as solutions, suspensions, and water-miscible semisolids are particularly preferred.

Each carrier must be "acceptable" in the sense of being compatible with the other ingredients in the formulation and not injurious to the patient. The carrier must be biologically acceptable and inert. In most cases, suitable buffers are included in the carriers to maintain the pH within the limits required to keep the drugs in solution. For example, for drugs containing a basic center, the solutions are buffered in the acidic pH range (approximately 2 to 6), and for drugs containing an acidic center, the solutions are buffered in the pH range (approximately 6 to 8). To prepare formulations suitable for intranasal administration, solutions and suspensions are sterilized and are preferably isotonic to blood.

In formulating a composition according to the present invention for the treatment of Alzheimer's disease, other drugs used in the treatment of AD, or agents useful in treating dementia (i.e., improving cognitive function), may be included. Preferred agents for use in combination with the folic acid according to the present invention for treating Alzheimer's disease include acetylcholine precursors (e.g., choline chloride and phosphatidyl choline (lecithin)); cholinergic agonists (e.g., acetylcholine, acetyl-L-carnitine, anatoxine a, arecoline, bethanecol, carbachol, decamethonium, 1,1-dimethyl-4-phenyl-piperazinium, cis-Dioxolane, epibatidine, epiboxidine, methacholine, methylcarbamylcholine, methylfurtrethonium, metoclopramide, muscarine, nicotine, oxotremorine, pilocarpine, and pharmaceutically acceptable salts thereof);

cholinesterase inhibitors (e.g., ambenonium, adrophonium, methylphysostigmine, neostigmine, pyridostigmine, and pharmaceutically acceptable salts thereof) and acetylcholinesterase inhibitors (e.g., physostigmine, tacrine (1,2,3,4-tetrahydro-9-aminoacridine), galanthamine, and pharmaceutically acceptable salts thereof).

In formulating a composition according to the present invention for the treatment of stroke, other drugs used in the treatment of stroke may also be included. Such additional drugs include, but are not limited to, anticoagulants, antiplatelet agents, calcium channel antagonists, and glutamate receptor antagonists. Preferred anticoagulants for use in the present invention include, but are not limited to, heparin, warfarin, and pharmaceutically acceptable salts thereof. Preferred antiplatelet agents for use in the present invention include, but are not limited to, aspirin, dipyridamole, and ticlopidine, and pharmaceutically acceptable salts thereof. Preferred calcium channel antagonists for use in the present invention include, but are not limited to, bepridil; calciseptine; cyproheptadine; diltiazem; flunarizine; fluspirilen; HA-1077; loperamide; nicardipine; nifedipine; niguldipine; nimodipine; nitrendipine; pimozide; ryanodine; verapamil; and pharmaceutically acceptable salts thereof. Preferred glutamate receptor antagonists (specifically the NMDA subtype) for use in the present invention include, but are not limited to: AP3, (±)-; AP4, (±)-; AP5, (±)-; AP5, D(-)-; AP7, (±)-; AP7, D(-)-; CGS 19755; 7-chlorokynurenic acid; CPP, (±)-; CPP,D-; dextromethorphan; dextrorphan; 5,7-dichlorokynurenic acid; 6,7-dichlorquinoxaline-2,3-dione (DCQX); 5,5-dimethyl-1-pyrroline-N-oxide; 5-fluroindole-2-carboxylic acid; HA-966, (±)-; HA-966, R(+)-; HA-966, S(-)-; ketamine; kynurenic acid; MDL 105,519; memantine; MK-801; 1-napthyl-acetyl spermine; pentamidine isethionate; and pharmaceutically acceptable salts thereof.

According to the present invention, the term "patient" will encompass any mammal requiring treatment with folio acid, or derivatives thereof, particularly a human patient suffering from an Alzheimer's disease, or at risk for Alzheimer's disease or stroke.

The dosage of folio acid or pharmaceutically acceptable salts thereof in the compositions of the invention will vary depending on several factors, including, but not limited to, the age, weight, and species of the patient, the general health of the patient, the severity of the symptoms, whether the composition is being administered alone or in combination with other agents, the incidence of side effects and the like. The desired dose may be administered as needed, and may be administered repeatedly over a period of months or years. Higher and lower doses may also be administered. A major advantage of the present invention is the extremely rapid onset of response, which enables the physician to adjust the dose to produce only the desired effects and nothing more, thereby optimizing drug use and minimizing side-effects.

The daily dose may be adjusted taking into account, for example, the above-identified variety of parameters. Typically, folio acid may be administered in an amount of up to about 60 mg/dose. Preferably, the amount of folic acid administered will not exceed 30 mg/dose. However, other amounts may also be administered, in particular, much smaller amounts of folio acid will be required when administered intranasally, in accordance with the present invention.

While it is possible for the active ingredient to be administered alone, as noted above, it is preferably present as a pharmaceutical formulation. The formulations of the present invention comprise at least one active ingredient, as defined above, together with one or more acceptable carriers thereof and optionally other therapeutic agents.

The method of the present invention may be practiced by administration of folic acid by itself or in a combination with other active ingredients in a pharmaceutical composition. Other therapeutic agents suitable for use herein are any compatible drugs that are effective by the same or other mechanisms for the intended purpose, or drugs that are complementary to those of folic acid. Such additional drugs include, but are not limited to, those drugs mentioned above in conjunction with treatment of Alzheimer's Disease or stroke.

The compounds utilized in combination therapy may be administered simultaneously, in either separate or combined formulations, or at different times than the folic acid, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

Having now generally described this invention, the same will be better understood by reference to certain specific examples, which are included herein for purposes of illustration only and are not intended to be limiting of the invention or any embodiment thereof, unless so specified. Set forth below are examples of experimental procedures designed to demonstrate the features of this invention in animal models, and examples of pharmaceutical dosage forms that embody and illustrate its reduction to practice.

EXAMPLE 1

Nasal Spray Solution

EXAMPLE 1

| NASAL SPRAY SOLUTION | |
| --- | --- |
| Folic acid | 60 mg |
| N-methylglucamine | 80 ml |
| Distilled water | 30 ml |

The folic acid is dissolved in 30 ml of the distilled water, N-methyl glucamine is added to adjust the pH of the solution to the final desired value (preferably between 4 and 8). The solution is placed in a nasal administrator designed to deliver 0.1 ml of spray for each application. One spray in each nostril will deliver a total of 0.4 mg of folic acid.

EXAMPLE 2

Nasal Gel (Aqueous)

| Folic acid | 200 mg |
| --- | --- |
| Methocel | 3 g |
| Distilled water | 100 g |
| Sodium hydroxide or sodium bicarbonate qs to adjust to the final desired pH. | |

Approximately 70 g of the water is heated to 80° C., and the methocel is dispersed in it with stirring. The folic acid is dissolved in 30 ml of distilled water, and concentrated sodium hydroxide solution is added to adjust the pH to the final desired value (preferably between 4 and 8). The resulting solution is heated to 80° C. and mixed with the methocel dispersion. The resultant mixture is allowed to stand at room temperature for 3 hours. The gel is placed in an ointment tube equipped with a fine orifice and is applied in the nasal nares with a finger or cotton tipped applicator.

EXAMPLE 3

Absorption of Folic Acid From the Nasal Cavity of Rats

These experiments determine the absorption of folic acid after nasal administration.

Surgical Technique

The nasal absorption of folic acid was measured using an in vivo technique in rats. Rats were fasted overnight prior to experimentation. Surgical procedures were performed under equithesin anesthesia (3 ml/kg, i.p.). An incision was made in the neck of each rat, and the trachea cannulated with polyethylene tubing (PF-260). A closed end tube was inserted through the esophagus to the posterior part of the nasal cavity to prevent drug from entering the esophagus. The nasopalatine passage was closed with an adhesive agent to prevent drainage of the drug from the nasal cavity to the mouth.

Formulation of the Intranasal Dosage Form

Fifty mg of folic acid was suspended in 10 ml of water and concentrated sodium bicarbonate solution was added dropwise until the folic acid was completely dissolved. The solution was filtered. The final pH was 8.3.

One-tenth ml of the above folic acid solutions was administered to four rats through the right nostril using a microsyringe. At 0, 2, 5, and 15 minutes following dosing, one rat was removed from the group, and the nasal cavity was thoroughly washed with 3 ml of water.

The concentrations of folic acid remaining in the nasal cavity were assayed using the spectrophotometric method described in USP XXII. The washings were placed in a spectrophotometer cell and the absorbance was measured. The concentration of folic acid remaining was calculated using the standard curve shown in FIG. 1, which is based on the data presented in Table 1.

TABLE 1

Standard Curve for Spectrophotometric Assay of Folic Acid

| Concentration (mg %) | Absorbance |
|---|---|
| 10 | 1.707 |
| 5 | 0.859 |
| 2.5 | 0.444 |
| 1.25 | 0.237 |
| 0.625 | 0.133 |

Results

The concentrations of folic acid found in the nasal cavities at various times following intranasal administration are shown in Table 2.

TABLE 2

Concentrations of Folic Acid in the Nasal Cavities of Rats at Various Times Following Intranasal Administration

| Time (min) | Concentration (mg %) |
|---|---|
| 0 | 4.1 |
| 2 | 3.8 |
| 5 | 2.9 |
| 15 | 2.6 |

These data show that folic acid is rapidly absorbed following intranasal administration. Following the 15-minute sample, the rat was examined, and little secretin was found in the nose, suggesting that the folic acid/sodium bicarbonate solution used was not irritating to the rat nasal mucosa.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A method for treating Alzheimer's Disease in a patient in need of such treatment comprising intranasally administering an effective amount of a pharmaceutical composition consisting essentially of folic acid, or a pharmaceutically acceptable salt thereof, and a pharmaceutically acceptable carrier therefor.

2. A method according to claim 1, wherein the carrier is aqueous.

3. A method according to claim 1, wherein the composition further comprises an cholinesterase inhibitor.

4. A method according to claim 3, wherein the cholinesterase inhibitor is selected from the group consisting of ambenonium, adrophonium, methylphysostigmine, neostigmine, pyridostigmine, and pharmaceutically acceptable salts thereof.

5. A method according to claim 3, wherein the cholinesterase inhibitor is an acetylcholinesterase inhibitor.

6. A method according to claim 5, wherein the acetylcholinesterase inhibitor is selected from the group consisting of tacrine, galanthamine, and pharmaceutically acceptable salts thereof.

* * * * *